United States Patent
Bartolucci et al.

(10) Patent No.: US 10,015,972 B2
(45) Date of Patent: Jul. 10, 2018

(54) BREADMAKING YEAST STRAINS WHICH ARE EFFECTIVE ON NON-SWEETENED OR SLIGHTLY SWEETENED DOUGHS

(71) Applicant: LESAFFRE ET COMPAGNIE, Paris (FR)

(72) Inventors: Jean-Charles Bartolucci, Hellemmes (FR); Evelyne Fonchy-Penot, Fleurbaix (FR); Ilknur Lagoutte Yalcin, Marcq-en-Baroeul (FR); Georges Parasie, Sequedin (FR); Dominique Petroff, Meudon (FR); Anne-Dominique Quipourt-Isnard, Marcq-en-Baroeul (FR); Valérie Trione, Comines (FR)

(73) Assignee: LESAFFRE ET COMPAGNIE, Paris (FR)

( * ) Notice: Subject to any disclaimer, the term of this patent is extended or adjusted under 35 U.S.C. 154(b) by 226 days.

(21) Appl. No.: 15/104,146

(22) PCT Filed: Dec. 8, 2014

(86) PCT No.: PCT/FR2014/053220
§ 371 (c)(1),
(2) Date: Jun. 13, 2016

(87) PCT Pub. No.: WO2015/092208
PCT Pub. Date: Jun. 25, 2015

(65) Prior Publication Data
US 2016/0316771 A1    Nov. 3, 2016

(30) Foreign Application Priority Data
Dec. 16, 2013  (FR) ..................... 13 62644

(51) Int. Cl.
*C12N 1/14* (2006.01)
*A21D 8/04* (2006.01)
*C12R 1/865* (2006.01)
*C12N 15/01* (2006.01)
*C12N 1/18* (2006.01)

(52) U.S. Cl.
CPC ............... *A21D 8/047* (2013.01); *C12N 1/18* (2013.01); *C12N 15/01* (2013.01); *C12R 1/865* (2013.01)

(58) Field of Classification Search
CPC ............ C12N 1/14; C12N 15/70; C12Q 1/44
USPC ..................... 435/254.21, 19, 471
See application file for complete search history.

(56) References Cited

FOREIGN PATENT DOCUMENTS

| EP | 0 511 108 A1 | 10/1992 |
|---|---|---|
| FR | 2 920 157 A1 | 2/2009 |
| WO | 97/28693 A1 | 8/1997 |
| WO | 2012/110711 A1 | 8/2012 |
| WO | 2014/060678 A1 | 4/2014 |

OTHER PUBLICATIONS

International Search Report for PCT/FR2014/053220 dated Feb. 12, 2015 [PCT/ISA/210].

*Primary Examiner* — Tekchand Saidha
(74) *Attorney, Agent, or Firm* — Sughrue Mion, PLLC

(57) ABSTRACT

The present invention relates to novel breadmaking yeast strains which are effective on non-sweetened and/or slightly sweetened products. It also relates to the yeasts obtained by a multiplication of the strains and also to the use thereof for the production of baked bakery products. The strains of the invention, selected after mutation in particular of a reference strain, are capable of multiplying according to a process that is slower than that of the reference strain, while exhibiting improved properties, in particular a fermentative capacity, compared with those of the reference strain.

10 Claims, No Drawings

BREADMAKING YEAST STRAINS WHICH ARE EFFECTIVE ON NON-SWEETENED OR SLIGHTLY SWEETENED DOUGHS

CROSS REFERENCE TO RELATED APPLICATIONS

This application is a National Stage of International Application No. PCT/FR2014/053220, filed on Dec. 8, 2014, which claims priority from French Patent Application No. 1362644, filed on Dec. 16, 2013, the contents of all of which are incorporated herein by reference in their entirety.

FIELD OF THE INVENTION

The present invention relates to novel *Saccharomyces cerevisiae* breadmaking yeast strains which are effective on non-sweetened and/or slightly sweetened doughs. It also relates to the yeasts obtained by multiplication of said strains and also to the use thereof for the production of baked bakery products.

TECHNOLOGICAL BACKGROUND

The consumption of non-sweetened and/or slightly sweetened breadmaking products is constantly on the increase. The production of these products uses breadmaking yeasts, termed baker's yeast, in dry, compressed or liquid form.

There are breadmaking yeast strains suitable for the various types of doughs: non-sweetened, slightly sweetened or strongly sweetened. Thus, the applicant proposes a complete range of yeasts intended for any type of breadmaking and for any baked bakery product.

However, yeast manufacturers are constantly in search of new yeast strains making it possible to produce yeasts which are even more effective, in particular in terms of fermentative capacities and of storage.

They are also constantly searching for an improved process for producing yeast, for instance improving production savings, which can be achieved by a higher productivity, by reducing production costs, by ease of implementation throughout the processes for producing yeast whatever the form: dry, compressed or liquid.

The robustness and regularity of the strain and also its resistance to drying are also properties that yeast manufacturers look for.

One of the reference strains of the applicant in this field is the one deposited on Feb. 12, 2003, with the CNCM (Collection Nationale de Cultures de Microorganismes [French National Collection of Microorganism Cultures], 26 rue du Docteur Roux, 75724 Paris cedex 15) under number I-2970. It is an important strain having multiple applications as dry yeast, as compressed yeast or as liquid yeast. Any improvement of this strain therefore has an impact on several products and qualities.

For a given strain and in light of the environmental conditions optimized in particular in terms of pH, of temperature, of fermentation medium, and of nitrogen (N) and phosphorus (P) resources, the most important parameter is the growth kinetics characterized by the evolution of the hourly multiplication rates and more globally the mean multiplication rate.

The mean multiplication rate is defined by $$\sqrt[d]{(Xend/X0)},$$

with
d=fermentation duration
Xend the amount of yeast at the end of fermentation
X0 the amount of yeast at the beginning of the fermentation.

It is known that increasing the mean multiplication rate has the effect of increasing the fermentative capacity of a yeast to the detriment of a loss of productivity.

Indeed, under industrial fermentation conditions for producing baker's yeast, the growth rate is controlled by the sugar feed flow rate according to a fed-batch fermentation technology and under aerobic conditions, thereby making it possible to optimize both the biomass production yield and the fermented productivity.

The limits of the industrial process regarding the mean multiplication rate occur at several levels:

Over the course of the first third of the fermentation, the hourly multiplication rate is controlled so as to remain below the critical multiplication rate in order to avoid the respiro-fermentative metabolism associated with ethanol production which penalizes the yeast biomass production yield from the sugar.

Over the course of the rest of the fermentation, and as the yeast biomass increases in the fermenter, the hourly multiplication rate is gradually reduced so as to not be at the limit of the oxygen transfer capacity and cooling capacity of the industrial fermenter.

Overall, the higher the hourly multiplication rates, the more the metabolism makes it possible to obtain yeasts rich in proteins including the enzymes which confer the fermentative power of the yeast.

If a yeast with a very high fermentative activity is sought, it is necessary to apply higher hourly multiplication rates, and therefore higher $O_2$ consumption rates and higher calorie production rates (rapid process). Consequently, the oxygen transfer and cooling capacities of the fermenter being what they are, it is necessary to reduce the amount of yeast in the fermenter and therefore to lose productivity.

One of the problems that the invention seeks to solve is therefore to provide at least one novel yeast strain having an improved fermentative activity compared with the reference strain I-2970 while at the same time being produced with a low mean multiplication rate (slow kinetics) and a productivity compatible with industrial and commercial use.

After multiple strain selection tests, the applicant has identified and selected a new strain which has an excellent fermentative activity while at the same time being produced by fermentation with slow growth kinetics, thereby making it possible to solve the problem mentioned above.

SUMMARY OF THE INVENTION

A subject of the invention is therefore novel yeast strains which, produced by fermentation with slower growth kinetics than those of the reference strain I-2970, make it possible to obtain baker's yeasts which have a fermentative activity in non-sweetened or slightly sweetened dough that is at least equal to that of the reference strain.

In particular, a subject of the invention is the strain deposited on Apr. 25, 2013, with the Collection Nationale de Cultures de Microorganismes [French National Collection of Microorganism Cultures], 26 rue du Docteur Roux, 75724 Paris cedex 15, under number I-4743.

A subject of the invention is also baker's yeasts, in dry, compressed or liquid form, which can be obtained by a multiplication of the I-4743 strain or by multiplication of any yeast strains derived from the I-4743 strain or the I-2970 strain and which have a fermentative activity greater than or equal to that of the I-2970 strain while at the same time being produced by fermentation with a slower growth kinetics activity.

The expression "derived strain" denotes a strain derived by any transformation whatsoever, for instance by one or more crosses and/or by mutation and/or by genetic transformation.

A strain derived by crossing can be obtained by crossing a strain according to the invention with the same strain, or with another strain according to the invention, or with any other strain.

A strain derived by mutation can be a strain which has undergone at least one spontaneous mutation in its genome or at least one induced mutation, for example induced by mutagenesis. The mutation(s) of the derived strain may or may not be silent.

The expression "mutagenesis" denotes both conventional mutagenesis obtained by radiation, for example using UV, or by mutagenic chemical agents, and insertional mutagenesis by transposition or by integration of an exogenous DNA fragment.

Mutagenesis by radiation comprises the use of UV, X-ray or gamma radiation.

The mutagenic chemical agents are, for example, EMS (ethylmethyl sulfonate), EES (ethylethyl sulfonate), nitrosoguanidine, nitrous acid, aflatoxin B1, hydroxylamine, 5-bromo-uracil, 2-aminopurine, proflavin and acridin orange.

A strain derived by genetic transformation is a strain into which an exogenous DNA has been introduced. This exogenous DNA is preferably provided by a plasmid or integrated directly into the genome.

A subject of the invention is also the baker's doughs obtained by a process comprising a step of fermentation of a baker's yeast according to the invention, and also the baked bakery products obtained.

DETAILED DESCRIPTION OF THE INVENTION

The object of the present invention is to provide at least one baker's yeast strain, giving, after industrial multiplication, a breadmaking yeast which has a fermentative activity in non-sweetened or slightly sweetened doughs that is greater than or equal to that obtained with the reference strain I-2970 while following growth kinetics that are slower than those of the reference strain.

The yeasts obtained by this "slow" production process can be provided in various forms: dry, compressed or liquid. They are resistant to production conditions, in particular to drying, and are stable with respect to storage.

The term "slightly sweetened dough (SD)" is intended to mean a baker's dough comprising less than 10% of added sugar.

The expression "rapid production process applied in the final step of industrial fermentation" is intended to mean a mean multiplication rate of greater than or equal to 1.17.

The expression "slow production process applied in the final step of industrial fermentation" is intended to mean a mean multiplication rate of less than or equal to 1.15.

The resistance to drying results in the maintaining, after drying, of a fermentative activity at least equal to 70% of the fermentative activity before drying.

The advantages of the strains of the invention also manifest themselves when yeasts obtained by culturing said strain are used as a fermentation agent in non-sweetened or slightly sweetened doughs.

The I-2970 strain is considered by the applicant to be a reference strain in the field to which the present invention relates. In its search for a solution to the problem mentioned above, the applicant was naturally interested in this strain, as a starting point, and also in the strains derived by mutation thereof.

The applicant first of all subjected the reference strain to a mutation in particular by UV radiation, followed by rigorous and reasoned selection among the thousands of mutants obtained.

Thus, the I-4743 strain was selected by the applicant as being the best solution to the problems mentioned above.

The selection process developed by the applicant is based, inter alia, on the following criteria taken separately or in combination:
  ability of the strain to assimilate the nitrogen present in the culture medium,
  amount of biomass produced,
  ferment power of the yeast obtained,
  loss of growth yield on sugar.

The selection process applied to the reference strain I-2970 comprises at least the following selection steps:
  Step I
  I.1) Mutagenesis of the reference strain I-2970 making it possible to obtain 10 000 mutant clones,
  I.2) screening of the 10 000 clones: two screenings carried out on a microplate scale (evaluation by assaying the ethanol in liquid medium) and two screenings carried out on a flask scale. The selection criteria retained in this step are:
    the amount of ethanol produced on liquid synthetic medium mimicking a normal dough must be greater than or equal to the amount of ethanol produced by the reference strain,
    the amount of biomass produced in the culture medium must be greater than or equal to the amount of biomass produced by the reference strain I-2970, and
    the fermentative capacity in non-sweetened dough must be at least 10% greater than the fermentative capacity of the reference strain of I-2970.

The culture medium developed specifically for screening the strains is a medium rich in nitrogenous molecules, this being for the purpose of eliminating as early as this first screening all the mutants which do not have a good ability to assimilate nitrogen.

Step I.2 makes it possible to select from 40 to 50 clones.
  Step II
  II.1) The clones retained in step 1.2 are studied in a 1-liter fermenter. The selection criteria are:
    the loss of growth yield on sugar must not be greater than 10% compared with the growth yield of the reference strain I-2970,
    the fermentative capacity in ND, which must be at least 10% greater than that of the reference strain.

Thus, about ten clones meeting the above criteria were selected.
  II.2) Study in 7-liter fermenter of the clones retained in step II.1. The selection criteria are:
    the growth yield on sugar must be at least equivalent to the yield obtained with the reference strain I-2970,
    the fermentative capacity must be at least 10% greater than that of the reference strain, and the nitrogen content of the yeast must be at least 5% greater than that of the reference strain.

Thus, one to two clones meeting the above criteria were selected.

Step III

III.1) Study of the clones selected in II.2 in a 20-liter fermenter. This includes a two-generation propagation of the parent yeast as is performed in a factory. The parent yeast is used to inoculate the "commercial" final fermentation, the reference strain I-2970 being produced under the same conditions. At the end of commercial fermentation, the yeast is separated and dehydrated. The evaluation criteria in this step are:

the absence of abnormality of the fermentation in the light of the parameters conventionally studied (kinetics, nutritive requirements, growth yield on sugar);

the fermentative capacity which must be 10% greater than that of the reference strain I-2970;

the nitrogen content which must be 5% greater than that of the reference strain I-2970.

The dehydrated and dried yeast in the form of instant dry yeast, generally denoted SPI, is then evaluated.

The evaluation criterion is the loss of fermentative capacity on drying, which must be less than or equal to 30%.

The dry yeast is also evaluated in various breadmaking recipes by measuring the proof time. The selection criterion is a proof time which must be 5% greater than that of the reference strain.

The selection process above made it possible to select the baker's yeast strain deposited on Apr. 25, 2013, at the Collection Nationale de Cultures de Microorganismes [French National Collection of Microorganism Cultures], 26 rue du Docteur Roux, 75724 Paris cedex 15, under No. I-4743, which constitutes the first subject of the present invention.

The selection process of the invention applied to the strains derived from the I-4743 strain makes it possible to also select other strains which correspond to the objective of the present invention, namely: providing new strains having a fermentative activity which is improved or at least identical to that of the reference strain I-2970 when the strains are produced by slow-process fermentation.

Another subject of the invention is therefore a strain derived from the I-2970 strain or from the I-4743 strain, characterized in that it meets the selection criteria of steps I, II and III described above.

The yeast strains of the invention are used for the production of breadmaking yeasts as described in the manual "*Yeast Technology*", 2nd edition, 1991, G. Reed and T. W. Nagodawithana, published by Van Nostrand Reinhold, ISBN 0-442-31892-8.

The production of baker's yeast comprises at least the first two steps of the set of following steps:

multiplication of a pure strain of baker's yeast in several stages, first under semi-anaerobic conditions, and then under aerobic conditions, separation of the baker's yeast thus produced from its culture medium, by centrifugation, with the obtaining of a liquid "yeast cream" containing approximately between 14% and 25% of dry matter, filtration of the liquid yeast cream thus obtained, generally after salting, on a rotary filter under vacuum, and obtaining of a dehydrated fresh yeast containing approximately 26% to 35% of dry matter, mixing of said dehydrated fresh yeast for the purposes of obtaining a very homogeneous mass, extrusion of the yeast thus obtained, either in the form of bars of compressed fresh yeast, or in the form of crumbled fresh yeast, sold at approximately 30% dry matter, or in the form of thin filaments if the yeast is intended to be dried, if the yeast is dried, the drying is preferably controlled rapid drying in the presence of an emulsifier, in particular sorbitan monostearate (SMS) at 1.5%. The drying is carried out in a stream of hot air, for example by fluidization of the yeast particles obtained by extrusion, vacuum-packaging of the dry yeast.

The yeast of the invention may be provided in the form of yeast creams, compressed yeasts and dry yeasts.

Generally, yeasts obtained by culturing the strain of the invention have:

a. a proof time in breadmaking which is shorter than that obtained with the breadmaking yeasts derived from the I-2970 strain, and/or b. a resistance to drying that is greater than or equal to that of the I-2970 strain.

Furthermore, they have a fermentative capacity in slightly sweetened dough that is from 2% to 6% and preferably from 3% to 5% greater than that obtained with the reference strain I-2970.

Another subject of the invention is a process for preparing non-sweetened or slightly sweetened baker's dough implementing a step of fermentation of a yeast such as that of the invention, and also the doughs and the baked bakery products obtained.

The following examples illustrate the invention without limiting the scope thereof.

EXAMPLES

The strains studied were evaluated in fermentation by virtue of their growth characterized by the mean multiplication rate, and the yeasts produced are evaluated by virtue of their nitrogen content, by virtue of their fermentative capacity and also by virtue of the fermentative capacity/nitrogen content ratio.

The fermentative capacity corresponds to the volume of $CO_2$ (in ml) produced by the yeast during fermentation in flour dough pieces. The fermentative capacity is measured using conventional techniques known to those skilled in the art, in particular by means of a fermentometer as described by Burrows and Harrison in "Journal of the Institute of Brewing", Vol. 65, 1959. In particular, the fermentative capacity is measured according to tests described in EP0511108 and U.S. Pat. No. 5,741,695 in the name of the applicant.

The fermentative capacity is measured on dough pieces consisting of 20 g of flour and of a yeast suspension, in a fermentometer of Burrows and Harrison type, over a period of 2 hours.

For measuring the fermentative capacity after culture in a medium rich in nitrogenous molecules, the yeast suspension consists of 100 mg of yeast dry matter in 15 ml of water containing 27 g/l of NaCl and 4 g/l of $SO_4(NH_4)_2$.

For measuring the fermentative capacity after fed-batch culture, the yeast suspension consists of 150 mg of yeast dry matter in 15 ml of water containing 27 g/l of NaCl and 4 g/l of $SO_4(NH_4)_2$.

In order to constitute the dough pieces, the mixture of flour and yeast suspension is mixed for 40 seconds in a kneader in order to obtain a dough which is then placed in a water bath at 30° C. 13 minutes after the mixing, the container containing the dough is hermetically sealed. The total amount of gas produced is measured in ml at 2 hours at 30° C.

The fermentative capacity is measured under various dough conditions:
  non-sweetened dough, the composition of which is that mentioned above (ND),
  sweetened dough containing 2 g of sucrose per 20 g of flour (SD), and
the difference in fermentative capacity of the strains tested compared with that of the reference strain, as a percentage, is calculated according to the following formula:

$$\frac{[(\text{fermentative capacity of the strain tested}) - (\text{fermentative capacity of the reference strain})]}{(\text{fermentative capacity of the reference strain})} \times 100$$

The nitrogen content is determined by the Kjeldahl method.

Example 1

Mutagenesis and First Screenings

The culture medium specifically developed for the screening is a medium rich in nitrogenous molecules, this being with the aim of verifying the capacity of the strains selected to assimilate a large amount of nitrogen.

The criteria applied for the selection are:
  the production of ethanol on liquid synthetic medium mimicking a normal dough. The amounts of ethanol produced by each mutant are compared with that produced by the reference strain,
  the production of $CO_2$ in a normal non-sweetened dough comprising 100 mg of yeast expressed as dry matter, per 20 g of flour, by comparing the amounts of $CO_2$ produced by each mutant with that produced by the reference strain,
  the amount of biomass produced on the medium developed for the screening, by comparing with the reference strain.

This step made it possible to select 40 to 50 strains having a biomass production at least identical to that of the reference strain cultured under the same conditions and a fermentative capacity in normal dough that is at least 10% greater than that of the reference strain.

Among the strains selected, the I-4743 strain stands out by virtue of: a biomass production that is 40% greater than that obtained with the I-2970 reference strain cultured under the same conditions, and also by virtue of a fermentative capacity in normal dough (ND) that is increased by 40% compared with that of the reference strain.

Example 2

Selection in a 1 Liter Fermenter:

The strains selected in example 1 were then studied in a 1-liter fermenter in fed-batch mode on synthetic medium in order to validate their ability to follow fermentation kinetics representative of baker's yeasts.

The scheme performed comprises a continuous sugar feed flow during the fermentation, and the nutrients are introduced as vessel heel.

After the production of the various strains, a biomass balance was carried out so as to retain only the strains not exhibiting nutritional deficiencies. The nitrogen content of the yeasts at the end of fermentation was also measured. The results obtained were then crossed with the fermentative capacities in normal non-sweetened dough.

This step made it possible to select several strains, among which the I-4743 strain stands out by virtue of:
  A loss of growth yield on sugar that is 10% lower compared with the growth yield of the reference strain.
  A fermentative capacity in ND that is 15% higher than that of the reference strain.

Selection in a 7-Liter Fermenter:

The best strains selected following the tests in a 1-liter fermenter were produced on molasses medium in a 7-liter fermenter according to a fed-batch scheme, the mean multiplication rate of which is 1.141.

This step made it possible to select several strains having:
  a growth yield at least equal to that obtained with the reference strain,
  a nitrogen content that is 8.5% higher relative to the yeast dry matter (YDM),
  a fermentative capacity on normal non-sweetened dough related to the nitrogen content of the yeast (ND/N) that is 5% greater than that obtained with the reference strain.

It emerges from these tests that the yeast produced with the I-4743 strain has a growth yield on sugar that is virtually equivalent to the reference strain and stands out by virtue of its capacities in ND and in 2 g-sweetened dough that are clearly higher than the I-2970 strain (+10% in ND and +3% in 2 g-SD). Moreover, this yeast has a higher nitrogen content (~9%/YS) than the reference strain. This observation reinforces the idea that this strain has an improved protein synthesis metabolism. The I-4743 strain also exhibits a clear advantage over the reference strain in terms of ferment power on normal dough related to the nitrogen content ND/N (ND/N of 21.7 compared with 20.6, i.e. +5%).

Example 3

The I-4743 strain was then tested in a 20-liter fermenter according to the following mode:
  two-generation propagation of the parent yeast. The parent yeast inoculates an entire series of fermentations of commercial yeast which are carried out in order to obtain yeasts with various protein contents by culturing them either on a rapid scheme or on a slow scheme,
  monitoring of the fermentation capacities conventionally studied (growth, nutrient requirements, final composition of the yeast, growth yield on sugar),
  evaluation of the quality of the commercial yeasts by measuring the ND fermentative capacity on a separation fermentometer, salting of the cream, dehydration on a rotary filter,
  the dehydrated yeast is homogenized with an emulsion composed of 12.5% SMS and 6% oil, so as to obtain an SMS content of 1.3% on the final dry yeast. After extrusion on a 0.6 mm perforation grid, the yeast undergoes batchwise fluidized-air drying on a Glatt dryer with a phase 1 temperature of 55° C. with dried air at 2 g of water/kg dried air, air flow rate of 30 $m^3$/h and phase 2 air temperature of 48° C., air flow rate of 30 $m^3$/h. The dry yeast is then vacuum-packaged,
  evaluation of the quality of the dry yeast by measuring the SC (dry matter content) and by virtue of the fermentative capacity in the ND and 2 g-SD fermentometer test. Evaluation of the storage of the dry yeast in a 14 d 43° C. test (storage for 14 days at 43° C.) by monitoring the ND fermentative capacity in a fermentometer.

The control is a dough obtained under the same conditions and with the same dough composition, other than the fact that it is inoculated with the yeast produced under the same conditions as the strains tested, but from the I-2970 reference strain.

The results obtained show that:
if a scheme with a slow mean multiplication rate (1.150) is applied, the I-4743 strain has a higher nitrogen content than that of the reference strain. Thus, I-4743 can reach a nitrogen content of 9%, whereas in comparison, the reference strain has, for slow kinetics of this type, difficulties in reaching a nitrogen content of 8.3%, which results in an improved fermentative capacity;
the fermentative capacity in normal dough/nitrogen content (ND/N) ratio makes it possible to compare the fermentative capacity between the two strains. The ratio of the I-4743 strain is higher than that of the I-2970 strain by more than 10% (ND/N of 22 compared with 19.5).

This shows that, with regard to the quantitative aspect, the protein synthesis by the I-4743 strain is greater than that by the I-2970 strain.

The post-treatment operations to obtain a dry yeast of good quality took place normally:
The cell size is not smaller than the reference strain, which penalizes neither the separation yield, nor the dehydration step on the rotary vacuum precoat filter with a normal dehydrated yeast with 31-32% SC.
The yeast after addition of the oil/SMS emulsion is neither tacky nor greasy, and therefore does not penalize the vermicelli extrusion step.
No extension of the drying time for obtaining a correct final content as % SC of 95.5%.
No abnormal color or odor observed on the dry yeast in the fresh state and after storage.
The dry yeast produced with the I-4743 strain with slow fermentation kinetics has an improved fermentative capacity on ND compared with that obtained with the I-2970 strain (+10% on average with a maximum of +22%).
Good drying ability of the I-4743 strain since the losses of capacity on drying are at the same level as the I-2970 strain, i.e. from −19% to −15% according to the tests without sugar or with a little sugar.

Fermentative Capacity Measured on the Dry Yeast After Storage:

The capacity losses linked to the storage (14 days at 43° C.) are comparable between the two strains: 15% of capacity loss after 14 days of storage at a temperature of 43° C.

Evaluation of the Strain in Breadmaking:

The dry yeasts produced with the I-4743 strain and the I-2970 strain were evaluated in breadmaking, according to the following implementation conditions.

The recipe used is expressed as baker's percentages, namely as weight of ingredients (in g) per 100 g of flour:

| Flour | 100% |
| Water | 65% |
| Salt | 2% |
| Dry yeast | 1.2% |
| Breadmaking improver | 1% |

The tests are carried out in a bakehouse at 22° C., with a flour that has been tempered at 22° C.

The test protocol applied is the following:
The dry ingredients are placed in a Mac Duffy® bowl of a Hobart A200® kneading machine, the jacket of which is prethermostated at 21.5° C., and are mixed on the first speed for 1 minute.
The pouring water at 20° C. is incorporated into the kneading machine.
Mixing is then carried out for 7 minutes on speed 1, followed by kneading for 1 minute 30 seconds on speed 2.
The dough is then immediately removed from the bowl and its temperature, which must be 25° C.+/−0.5° C., is measured.
The dough is directly divided into dough pieces of 320 g, and then rolled into not very tight balls and the balls are left to stand under a cover.
35 minutes after the end of the kneading, the dough pieces are mechanically shaped, and are placed in molds (dimensions: base of the mold of 185×75 mm; top of the mold of 200×90 mm; height of the mold of 75 mm), which are themselves placed in a Stericult® incubator, the setpoints of which are regulated at 35° C. and 90% ERH.
The proof time, which is the time between the moment the molds are placed in the incubator and the moment the dough reaches a height of 85 mm in the mold, is then measured.
After one hour of proof in the incubator, some of the molds are placed in a ventilated Angoulvant rotary rack oven for 22 minutes at 205° C.

One of the most advantageous indicators in terms of performance level is the proof time, measured in minutes. The table which follows indicates the proof times obtained with the dry yeasts produced with the two strains, depending on whether the multiplication scheme is slow or rapid. The ranges of values obtained, according to various tests, are indicated.

| | | Strain | |
| --- | --- | --- | --- |
| | | I-4743 | I-2970 |
| Scheme | Slow | 75-81 | 84-86 |
| | Rapid | 72-81 | 78-83 |

Proof time ranges obtained during various tests, in breadmaking.

It is observed that, in the slow scheme, the performance levels obtained with the I-4743 strain are at the level of those obtained with the I-2970 reference strain in the rapid scheme.

The invention claimed is:
1. A *Saccharomyces cerevisiae* yeast strain deposited on Apr. 25, 2013, with the CNCM under number I-4743.
2. A *Saccharomyces cerevisiae* yeast strain deposited on Apr. 25, 2013, with the CNCM under number I-4743, selected according to the following selection process:
   a. Mutagenesis of the reference strain deposited at the CNCM under number I-2970,
   b. After culture on culture medium rich in nitrogenous molecules, of the mutants obtained in step a), the mutants of which the yeast obtained has a fermentative capacity on non-sweetened dough that is at least 10% greater than that of the yeast derived from the reference strain are retained, c. After fed-batch culture in a 1-liter fermenter of the mutants selected in step b), the mutants in which:
   the loss of growth yield on sugar must not be 10% greater compared with the growth yield of the I-2970 reference strain,
   the fermentative capacity in normal dough of the yeast obtained must be at least 10% greater than that of the reference strain,
   are retained, d. After fed-batch culture, in a 7-liter fermenter, of the mutants selected in step c, the mutants in which:
   the growth yield on sugar is at least equivalent to the yield obtained with the I-2970 reference strain,
   the fermentative capacity of the yeast obtained is at least 10% greater than that of the reference strain, and
   the nitrogen content of the yeast obtained is at least 5% greater than that of the reference strain,
   are retained, e. After fed-batch culture without abnormality, in a 20-liter fermenter, of the mutants selected in step d, the mutants of which the yeast obtained has:
   a fermentative capacity that is 10% greater than that of the reference strain, and
   a nitrogen content that is 5% greater than that of the reference strain, are finally retained.

3. A baker's yeast obtainable by culturing the strain as claimed in claim 2, having:
   a. a proof time in breadmaking which is less than that obtained with the breadmaking yeasts derived from the I-2970 strain, and/or
   b. a resistance to drying greater than or equal to that of the I-2970 strain.

4. The baker's yeast as claimed in claim 3, characterized in that it has a fermentative capacity in slightly sweetened dough that is from 2% to 6% and preferably from 3% to 5% greater than that obtained with the I-2970 reference strain.

5. The baker's yeast as claimed in claim 3, characterized in that it is in a liquid, semi-liquid, compressed or dry form.

6. A process for preparing a baker's dough, comprising a fermentation step with a yeast as claimed in claim 3.

7. A baker's dough obtained according to the process of claim 6.

8. The baker's dough as claimed in claim 7, characterized in that it is a non-sweetened or slightly sweetened dough.

9. A process for preparing a baked breadmaking product, comprising a step of baking a baker's dough obtained according to the process of claim 6.

10. A breadmaking product obtainable by the process as claimed in claim 9.

* * * * *